(12) United States Patent
Pugia et al.

(10) Patent No.: US 9,366,669 B2
(45) Date of Patent: Jun. 14, 2016

(54) COATED SUBSTRATES FOR HIGH ENERGY CAPTURE PHASE BINDING AND METHODS OF PRODUCTION AND USE THEREOF

(71) Applicant: Siemens Healthcare Diagnostics Inc., Tarrytown, NY (US)

(72) Inventors: Michael J. Pugia, Granger, IN (US); Pratap Singh, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/364,850

(22) PCT Filed: Dec. 20, 2012

(86) PCT No.: PCT/US2012/070763
§ 371 (c)(1),
(2) Date: Jun. 12, 2014

(87) PCT Pub. No.: WO2013/096528
PCT Pub. Date: Jun. 27, 2013

(65) Prior Publication Data
US 2014/0336084 A1 Nov. 13, 2014

Related U.S. Application Data

(60) Provisional application No. 61/578,043, filed on Dec. 20, 2011.

(51) Int. Cl.
*G01N 15/06* (2006.01)
*G01N 33/00* (2006.01)
*G01N 33/48* (2006.01)
*G01N 33/543* (2006.01)

(Continued)

(52) U.S. Cl.
CPC ....... *G01N 33/54306* (2013.01); *B01J 19/0046* (2013.01); *C40B 60/12* (2013.01); *G01N 33/54393* (2013.01); *B01J 2219/0063* (2013.01); *B01J 2219/00628* (2013.01); *B01J 2219/00637* (2013.01); *B01J 2219/00648* (2013.01); *B01J 2219/00659* (2013.01)

(58) Field of Classification Search
CPC ........ G01N 15/06; G01N 33/00; G01N 33/48
USPC ............. 422/50, 68.1, 502, 503, 504; 436/43, 436/174
See application file for complete search history.

(56) References Cited

U.S. PATENT DOCUMENTS 5,474,796 A  12/1995  Brennan
5,510,270 A   4/1996  Fodor et al.
(Continued)

OTHER PUBLICATIONS

International Search Report and Written Opinion of International Application No. PCT/US2012/070763 dated Apr. 5, 2013.
(Continued)

*Primary Examiner* — Brian J Sines
(74) *Attorney, Agent, or Firm* — Noam R. Pollack (57) ABSTRACT

A substrate, which is useful for performing biological, chemical and diagnostic assays, and a method for preparing the substrate are provided. The substrate has an upper surface with a coating disposed thereon. The coating comprises a charged polymer, a non-ionic polyether, and a silicate compound. The substrate can increase capture phase binding and reduce non-specific binding of biomolecules for a biological microarray.

19 Claims, 2 Drawing Sheets

Comparison of coated and uncoated bound glass surfaces

Bound glass    Bound glass cellulose 4    Bound glass cellulose 4 coated KOK/PDDA Bound glass cellulose 3 coated KOK/PDDA    Bound glass cellulose 3 coated KOK/PADDXA    Bound glass cellulose 3

(51) Int. Cl.
  *C40B 60/12* (2006.01)
  *B01J 19/00* (2006.01)

(56) References Cited

U.S. PATENT DOCUMENTS

| | | |
|---|---|---|
| 5,807,522 A | 9/1998 | Brown et al. |
| 6,083,708 A | 7/2000 | Singh et al. |
| 6,271,278 B1 | 8/2001 | Park et al. |
| 6,773,928 B1 | 8/2004 | Yin et al. |
| 7,547,556 B2 * | 6/2009 | Hunter et al. ............ 436/180 |
| 7,682,565 B2 * | 3/2010 | Linton et al. ............ 422/68.1 |
| 7,799,553 B2 * | 9/2010 | Mathies et al. .......... 435/283.1 |
| 8,105,554 B2 * | 1/2012 | Kanigan et al. ........... 422/504 |
| 8,431,340 B2 * | 4/2013 | Jovanovich et al. ........ 435/6.1 |
| 2005/0019828 A1 | 1/2005 | Qiao et al. |
| 2006/0057209 A1 | 3/2006 | Chapman et al. |
| 2006/0121474 A1 | 6/2006 | Kim et al. |

OTHER PUBLICATIONS

Katzur et al., "Surface-immobilized PAMAM-dendrimers modified with cationic or anionic terminal functions: Physicochemical surface properties and conformational changes after application of liquid interface stress", Journal of Colloid and Interface Science, vol. 366, Issue 1, Jan. 15, 2012, pp. 179-190.

European Search Report and Search Opinion of European Application No. 12860149.9 dated Nov. 27, 2015.

* cited by examiner

Figure 1. Comparison of spotting methodolgy

Visual result 100 nL pin
spotted membrane 20 nL piezo
spotted membrane 100 nL piezo
spotted membrane Figure 2. Comparison of coated and uncoated bound glass surfaces

COATED SUBSTRATES FOR HIGH ENERGY CAPTURE PHASE BINDING AND METHODS OF PRODUCTION AND USE THEREOF

CROSS REFERENCE TO RELATED APPLICATIONS

The entirety of U.S. Provisional Application Ser. No. 61/578,043, filed on Dec. 20, 2011, is hereby expressly incorporated herein by reference.

STATEMENT REGARDING FEDERALLY SPONSORED RESEARCH OR DEVELOPMENT

Not applicable.

BACKGROUND OF THE INVENTION

1. Field of the Invention

The presently disclosed and claimed inventive concept(s) relates generally to substrates useful for performing biological, chemical and diagnostic assays as well as methods of producing and using same.

2. Description of the Background Art

Microarray technology has emerged as a powerful tool in life science and biomedical research. Microarrays are excellent tools for testing a large number of known different molecules against unknown substances. A microarray usually consists of a solid support (such as a glass slide, silicon wafer, and nylon- or polymer-based substrate) that contains numerous different reagents immobilized on its surface in a pre-arranged manner. These reagents (known as probes, capture phases or capture agents) are usually selected for their high specialty and reactivity, such as binding, affinity, toward their counterparts (known as targets) found in biological samples. After applying a biological sample onto a microarray under an experimentally-controlled condition, the interactions between each probe on a microarray and its corresponding target in the biological sample can be observed through various target labeling techniques and appropriate detection instrumentation, thereby providing the microarray use with qualitative and quantitative information about the target in the tested biological sample.

Microarrays can be synthesized on a substrate according to an assortment of methods. For example, to produce a microarray directly on a substrate, one may employ methods of solid-phase chemical synthesis in combination with site-directing mass as disclosed in U.S. Pat. No. 5,510,270. Alternatively, one may use photolithographic techniques involving precise drop deposition via piezoelectric pumps, as disclosed in U.S. Pat. No. 5,474,796, incorporated herein by reference. Or, one may contact a substrate with typographic pins holding droplets and using ink jet printing mechanisms to lay down a microarray matrix as disclosed in U.S. Pat. No. 5,807,522, incorporated herein by reference.

Background binding of proteins, carbohydrates, cell lysates and the like to the surface of glass or other substrates employed in a microarray which include microspots containing protein capture agents or the like has posed a problem for a number of years. Non-specific binding of proteins to a microarray substrate increases the background noise when the microarray is imaged or the signals generated on the microspots are otherwise read; this makes it difficult to detect and distinguish signals being obtained from labels which should be specifically bound to particular spots, particularly in instances where the signal is relatively weak, because such background noise interferes and prevents obtaining precise readings.

A common method being used to lower non-specific binding involve manners of blocking the regions of the surface of the substrate surrounding each of the plurality of microspots after capture phase binding. The blocking method comprises contacting the surface with a charged polymer or a compound that has good non-specific binding itself after attachment of a capture phase but before a detection step, such as, contacting the microarray with a target moiety. The charged compound negates a substrate surface of an opposite charge. It cancels and masks the influence of the substrate. However, this process can reduce affinity reactions between affinity phase and sample. The problem with the current state of the art is that typically higher binding of the capture phase leads to greater non-specific binding.

Adhesion of a capture phase to a surface is related to the surface energies and the electrostatic charges of the surface and the capture phase. Surface energies depend on hydrophilic and hydrophobic nature of the materials. Electrostatic charges depend on the charge densities and counter charges between the capture phase and the surface. Unfortunately, the factors affecting binding of a capture phase to a surface are the same ones affecting non-specific binding of a protein to the surface.

Thus, it is an object of the presently disclosed and claimed inventive concept(s) to provide a substrate having a high binding of a capture phase and low non-specific binding, and a microarray using such a substrate, that overcomes the defects and disadvantages of the prior art.

DETAILED DESCRIPTION OF THE INVENTIVE CONCEPT(S)

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses and chemical analyses.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The presently disclosed and claimed inventive concept(s) relates to an improved substrate having increased capture phase binding and reduced non-specific binding. The substrate comprises a support having a coating applied to an upper surface thereof. In one embodiment, the coating may be applied substantially uniformly to the upper surface of the support. The support may be formed of a material suitable for use as described herein or as otherwise contemplated in the art. For example but not by way of limitation, the support may be utilized for fabricating a biological microarray and may be constructed of glass, plastics, membrane (paper or composite) and any other material (or combination of materials) used for fabricating microarrays. The membrane can be made of glass, cellulose, glass cellulose, or other materials.

The coating comprises a charged polymer, a non-ionic polyether polymer and a silicate compound. The charged polymer can be an anionic polyelectrolyte polymer ($\alpha$), a cationic polyelectrolyte polymer ($\beta$), and/or a zwitterionic polyelectrolyte polymer ($\alpha,\beta$).

The anionic polyelectrolyte includes polymer molecules, each containing a plurality of negatively charged ionic groups. The polymer molecules may have a straight or branched main chain (back-bone), and the ionic groups may be present in the main chain or as pendent groups of the main chain. The anionic groups can be selected among existing anionic groups, such as carboxylate groups, sulphate groups, sulphonate groups, phosphate groups and phosphonate groups. The main polymer chain may contain different types of polymerizable monomers, such as but not limited to, vinyl alcohol, isocyanate, (meth)acrylate, acrylamide, alkylene oxide, alkylene oxide adducts, carbohydrates (such as, but not limited to, cellulose and cellulose derivatives), and combinations thereof. The anionic polyelectrolyte polymer can be phosphates, carbonates, and sulfonates polymers in ionized forms.

Examples of the anionic polyelectrolyte polymer include, but are not limited to, polyacrylic acids (PAA), poly-(sodium-4-styrenesulfonates) (PSS), polymethacrylic acids (PMA), polymethacrylic methacrylates (PMMA), anionic polyacrylamide, poly(2-acrylamido-2-methyl-1-propane sulfonic acid) (PAMPS), sulfonated poly(ether ether ketone) (SPEEK), poly(ethylenesulfonic acid), poly(methacryloxyethylsulfonic acid), their salts, and copolymers thereof.

The cationic polyelectrolyte polymer denotes a high molecular weight polymeric material having, as part of its chemical structure, a plurality of positively charged chemical groups. In one embodiment, the cationic polyelectrolyte polymers have a plurality of ammonium groups that provide the positive charges. Such ammonium groups are either the protonated form of a primary, secondary or tertiary amine, or are quaternary ammonium groups.

The cationic polyelectrolyte polymers are typically prepared by either polymerizing amine-containing polymerizable monomers, or by converting an existing high molecular weight material into an amine-containing material. Two well-known cationic polyelectrolyte polymers that are made by polymerizing an amine-containing monomer are polyethylenimine (PEI) and poly(diallyldimethylammonium chloride)

(PDDA), which are the polymerization product of ethyleneimine and diallyldimethylammonium chloride, respectively.

Also suitable for use in the presently disclosed and claimed inventive concept(s) is the polymerization product of diallyldialkylammonium anions other than diallyldimethylammonium chloride, where other suitable anions include bromide and acetate, and where other suitable alkyl groups include ethyl, n-propyl, i-propyl, n-butyl, i-butyl, t-butyl, etc. 2-Vinylpyridine (2-VP) and 4-vinylpyridine (4-VP) are two monomers that have been polymerized to form a cationic polyelectrolyte polymer, i.e., poly(2-vinylpyridine) and poly(4-vinylpyridine) respectively, although these monomers could also be used in a copolymerization process to produce a cationic polyelectrolyte polymer.

Allylamine may be polymerized to form poly(allylamine hydrochloride), and vinylamine may be polymerized to form polyvinylamine. Related suitable cationic polyelectrolyte polymers are polyamidoamines modified by grafting onto ethyleneimine, polyamidoamines, polyetheramines, polyvinylamines (PVA), modified polyvinylamines, polyalkylamines, polydimethylaminostyrene, polyvinylimidoazoles, and polydiallydialkyl ammonium halides, in particular polydiallyldimethylammonium chloride.

Other examples of cationic polyelectrolyte polymers include, but are not limited to, polyvinylpyrrolidone (PVP), poly(acrylamide) (PAamide), poly(acrylamide-co-diallyldimethylammonium chloride) (PADDA), poly(vinylbenzyltrimethylammonium) (PVBTA), ionenes, poly(acryloxyethyltrimethyl ammonium chloride), poly(methacryloxy (2-hydroxy)propyltrimethyl ammonium chloride), poly(N-alkylvinylpyridines), poly(allylaminehydrochloride) (PAH) polysulfoniums, polyphosphoniums and copolymers thereof.

The cationic polyelectrolyte polymer may be a blocking protein. Blocking proteins are useful for blocking non-specific binding. Examples of blocking protein that may be utilized in accordance with the presently disclosed and claimed inventive concept(s) include, but are not limited to, BSA (bovine serium albumin), milk proteins, casein, an albumin in a quaternary form with counter anion, and combinations thereof.

The zwitterionic polyelectrolyte polymer comprises a repeat unit that has both a negative charge and a positive charge. Such repeat units are termed "zwitterionic", and the polyelectrolyte is termed a "zwitterionic polyelectrolyte." Though zwitterionic repeat units contribute an equal number of positive and negative repeat units, the zwitterionic group is still solvated and relatively hydrophilic. One non-limiting example of a zwitterionic polyelectrolyte polymer is poly(2-acrylamideo-2-methyl-1-propanesulfonic acid) (PAM PSA).

The non-ionic polyether comprises groups that are rich in oxygen, and said non-ionic polyether is a common blocking polymer. Examples of the non-ionic polyether include, but are not limited to, poly(ethylene glycol) (PEG), polypropylene glycol (PPG), PEG-PPG block copolymers, PEG-PPG copolymers, PEG-PPG-PEG triblock polymers, polycarbonate polyether glycol (KOK), ethylhydroxyethylcellulose (EHEC), polymerized allyl-glycidyl ether, and polymerized phenyl glycidyl ether.

A silicate compound contains a negatively charged silicate ($SiO^-_2$) group. The silicate containing solution has a pH of about 11.3. The silicate compound may be metal silicates or alkyl silicates. The metal silicates can be alkali metal silicates. In one non-limiting embodiment, the silicate compound is sodium silicate.

The supports for use in the presently disclosed and claimed inventive concept(s) may flexible or rigid, and may include (for example but not by way of limitation) glass, metal, silicon wafer, membrane, plastic film, and combinations thereof. Glass, or fused silica, is the most commonly used microarray support in the art, although plastics, metals, and semiconductors may also be used in accordance with the presently disclosed and claimed inventive concept(s). Plastic film may be (for example but not by way of limitation) nylon, nitrocellulose, silicone, polyformaldehyde, cellulose, cellulose acetate, polyethylene, polypropylene, polystyrene, and the like. In one non-limiting embodiment, the support is a membrane which comprises at least one material selected from glass, cellulose, and glass cellulose fibers. In the presently disclosed and claimed inventive concept(s), the terms of "membrane", "paper" and "composite" are the same and exchangeable.

The presently disclosed and claimed inventive concept(s) relates to a method of preparing a substrate with increased capture phase binding and reduced non-specific binding when compared to an untreated substrate. The method includes applying a coating composition (as described in detail herein above) to an upper surface of a support (as described in detail herein above) and drying the coated layer. The coating composition may be applied in a substantially uniform manner to the upper surface of the support. The support may be constructed of any materials that allow the support to function in accordance with the presently disclosed and claimed inventive concept(s), such as but not limited to, glass, membrane (formed of glass, cellulose, glass cellulose fibers, etc.), plastic and other materials known for making microarrays. In one embodiment, the membrane based on glass and cellulose fibers are made on paper making machines using a wire mesh. The surface that touches the wire mesh is "rough" to the touch. The surface away from the wire mesh is "felt" to the touch.

The coating composition comprises a mixture of a charged polymer, a non-ionic polyether, and a silicate compound. The mixture is dissolved in water. The charged polymer can be an anionic, a cationic, or a zwitterionic polyelectrolyte polymer. The polyelectrolyte polymers, the non-ionic polyether and the silicate compounds are the same as those described herein previously.

In one embodiment, the amounts of the charged polymer can be in the range of about 180 μL to about 4500 μL, the amounts of the non-ionic polyether can be in the range of about 120 μL to about 3000 μL, and the amounts of the silicate compound can be in the range of about 360 μL to about 9000 μL. In another embodiment, the amounts of the charged polymer can be in the range of about 300 μL to about 2700 μL, the amounts of the non-ionic polyether can be in the range of about 200 μL to about 1800 μL, and the amounts of the silicate compound can be in the range of about 600 μL to about 5400 μL. The coating mixture is applied on the upper surface of the support. Then the surface of the support is dried in an oven with air flow. For example but not by way of limitation, the drying step may be carried out in an oven at a temperature of about 90° C. and with air flow for about 5 minutes.

For a non-ionic polyether insoluble in water, a method of preparing a substrate comprises: providing an upper surface of a support; applying a first coating composition to the upper surface to obtain a first coating; drying the first coating; applying a non-ionic polyether soluble in ethanol to the first coating to obtain a second coating; and drying the second coating. The first coating composition comprises a charged polymer and a silicate compound. The charged polymers, the non-ionic polyethers and the silicate compounds are the same as those described herein previously. For example but not by way of limitation, the drying steps may be carried out in an oven at a temperature of about 90° C. and with air flow for about 5 minutes.

The presently disclosed and claimed inventive concept(s) also relates to a biological microarray formed by the attachment of biomolecules to the substrate described herein above. Biomolecules for a microarray are immobilized on the substrate by any method known in the art or otherwise contemplated herein, including but not limited to, chemical interactions, electrostatic interactions, or combinations thereof. According to the presently disclosed and claimed inventive concept(s), one may attach several kinds of molecules to create assorted biological microarrays. The biomolecules may exhibit specific affinity for another molecule.

In one embodiment of the presently disclosed and claimed inventive concept(s), a dendrimer is used as a capture phase or capture agent attached to the substrate described herein above. Dendrimers are highly uniform, three-dimensional, monodisperse polymers with a tree-like, globular structure. A dendrimer is a substantially or completely symmetrical, layered macromolecule that includes three distinct areas: the polyfunctional central core or focal point, various radial layers of repeating units (so-called generations G), and the end groups, which are also termed peripheral or terminal groups.

Dendrimers are well defined, highly branched macromolecules that emanate from a central core. They are a unique class of nanoscopic synthetic macromolecules and allow controlled architecture, low polydispersity and defined molecular mass. These molecules contain a very large number of reactive terminal functional groups that have been utilized to covalently couple a large variety of molecules, including proteins.

Examples of suitable dendrimers include, but are not limited to, polyamidoamine ("PAMAM") dendrimers. In one embodiment, a fifth generation STARBURST™ dendrimer with ethylenediamine core and amine terminal (E5) is used. This dendrimer has a molecular mass of 28,860 Da with 128 terminal amino groups and an estimated particle diameter of 7.0 nm.

Streptavidin has traditionally been used as an affinity tag because it binds biotin with high affinity ($K_d=10^{-14}$ M) and specificity. Streptavidin will bind biotinylated compounds (such as but not limited to, proteins and nucleic acids) under physiological conditions, and the bound compounds can be subsequently eluted with biotin. In one embodiment of the presently disclosed and claimed inventive concept(s), streptavidin is used as an affinity label on capture phases. Streptavidin binds to biotin conjugated to molecules to be captured.

Measurement Methods

Measurement of Surface Energy: The surface energy (hydrophilicity) is measured by applying a 4 µL of water droplet to the coated glass surface with digital contact angle measurement equipment. A VCA optima contact angle meter is used for measuring the surface energy in the presently disclosed and claimed inventive concept(s). The change in surface energy is calculated by comparison of coated to uncoated glass. An increase change means the coating makes the surface more hydrophilic.

Measurement of Electrostatic Binding Strength: Negative electrostatic binding to membranes can be measured by staining with tetrabromophenol blue (TBPB). Duplicate 3/16" circles of the membrane are punched and placed into separate wells of a 96-well ELISA (enzyme linked immunosorbent assay) plate. The dye solution is made at 250 mg in 70 mL water with 10 mL ethanol. To each well, 200 µL of TBRB solution is added, and the plate is shaken for 10 minutes, after which the dye is removed, and the plate is washed two times with 200 µL PBS (phosphate buffer saline, pH 7.4). The plate is then shaken for 10 minutes at RT (room temperature). The absorbance of the dye bound to the paper circle is read at 580 nm over 900 nm.

Positive electrostatic binding to membranes can be measured by staining with methylene blue. Duplicate 3/16" circles of the membrane are punched and placed into separate wells of a 96-well ELISA plate. The dye solution is made at 250 mg in 70 mL water with 10 mL ethanol. To each well, 10 µL of methylene blue solution is added and the plate is shaken for 10 minutes at RT, after which the dye is removed and the plate is washed 2 times with 200 µL PBS with plate shaken for 10 minutes at RT. The absorbance of the dye bound to the paper circle is read at 580 nm over 900 nm.

Measurement of Protein Binding Strength: A spot of 10 µL of Streptavidin (0.010 m/mL or 14.27 µM) is pipetted onto three 3/16" circles of the membrane punched and placed into separate wells of a 96-well ELISA plate. The wells of the plate are washed two times with 200 µL PBS with plate shaken for 10 minutes at RT. A spot of 10 µL of ALP-Biotin is pipetted onto the washed circles of membrane and the plate is shaken for 10 minutes at RT. The ALP-Biotin (0.040 mg/mL or 0.25 µM) is dissolved in a solution (25 mM Tris, 25 mM HEPES, 3.75% BSA, 0.1 M NaCl, 10% Trehalose, 2.5 mM magnesium acetate and 0.5 mM zinc chloride, adjusted to pH 7.5). The amount of ALP-Biotin bound to the Stretavidin is measured by adding 100 µL of A and B of Sigma Alk Phos Red Microwell Substrate. The color is read at 490 nm (IR absorbance at 900 nm) between 1-10 min after addition of red substrate using an ELISA plate reader. The absorbance is directly proportional to the amounts of Streptavidin bound on top of the membrane.

Capture Binding and Capture Phase Activity: A spot of 10 µL ALP-Biotin:Streptavidin-dendrimer is pipetted onto three 3/16" circles of the membrane punched and placed into separate wells of a 96-well ELISA plate. The ALP-Biotin (0.040 mg/mL or 0.25 µM) is mixed with Streptavidin-dendrimer (0.428 mg/mL or 14.45 µM) in a spotting solution and incubated >5 min before spotting. The spotting solution has 25 mM Tris, 25 mM HEPES, 3.75% BSA, 0.1 M NaCl, 10% Trehalose, 2.5 mM magnesium acetate and 0.5 mN zinc chloride, adjusted to pH 7.5.

The wells of the ELISA plate are washed three times with 200 µL PBS. The bound ALP-Biotin:Streptavidin-dendrimer is measured by adding 10 µL of para-nitrophenol phosphate (One Step PNPP, 10 mM, 31.7 µg/10 mL in 28 mM sodium borate buffer at pH 8.5) and followed by addition of 170 µL of 28 mM sodium borate buffer at pH 8.5. The hydrolysis of the PNPP substrate results in a yellow color. The color (Light Output) is read and the absorbance is directly proportional to the amounts of ALP bound top of the membrane. In all cases the 96-well ELISA plate used is Costar cat #9107 EIA plate with flat bottom and medium binding.

EXAMPLES

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

Example 1

Coating of Membrane

A coating solution was prepared by mixing 20 ml RO-DI water with 900 µL charged polymer, 600 µL non-ionic polyether polymer (PEG) and 1800 µL sodium silicate (10.8% $NaO_2$ and 26.5% $SiO_2$). The mixture was stirred to dissolve all the ingredients to make a coating solution. The coating solution was applied to the surface of a glass cellulose membrane. The membrane was then dried in an oven at the temperature of about 90° C. and with air flow for about 5 minutes. A second coating of 3 mL/dL of non-ionic polyether polymers in ethanol over the membrane was carried out when polycarbonate KONK and polypropyl glycol were used as non-ionic polyether polymers. The second coating was dried in the oven at the temperature of about 90° C. with air flow for 5 minutes. Various charged polymers and non-ionic polyethers were used to make the coatings over the surfaces of glass cellulose membranes. Negative electrostatic binding, positive electrostatic binding, protein binding and capture phase activity (light output) were measured on the coated membranes based on the measurement methods described previously. The effects of the coating composition on the glass cellulose membrane are listed in Table 1, in which SD represents standard deviation and CV represents coefficient of variance.

The results in Examples 1 and 2 indicate that light outputs (promotes capture phase binding) of using anionic ($\alpha$), cationic ($\beta$) and zwitterionic ($\alpha\beta$) polyelectrolyte polymers are all increased. Anionic ($\alpha$) polyelectrolyte polymers give the most increase. Cationic ($\beta$) polyelectrolyte polymers increase the light outputs or promote capture phase bindings. These results are unexpected as the dendrimer capture phase is positively charged and should not be bound to cationic ($\beta$) polyelectrolyte polymers. However, these cationic ($\beta$) polyelectrolyte polymers are in quaternary forms with counter anions that can bind to the dendrimer. Anionic ($\alpha$) and non-anionic polyelectrolyte polymers reduce the electrostatic bindings of negative molecules but increase the positive electrostatic bindings of positive molecules.

Positive electrostatic bindings directly correlate to protein bindings. Cationic ($\beta$) and zwitterionic ($\alpha\beta$) polyelectrolyte

TABLE 1

| Charged polymer | Non-ionic polyether | Sodium silicate | Negative electrostatic binding Ave | Negative electrostatic binding SD | Positive Electrostatic binding Ave | Positive Electrostatic binding SD | Increase in surface energy dynes/cm | Protein binding change from uncoated % | Increased light output % | CV % |
|---|---|---|---|---|---|---|---|---|---|---|
| PAA($\alpha$) | none | none | 0.19 | 0.01 | 2.92 | 0.06 | 12.5 | 18 | 28 | 9 |
| PSS($\alpha$) | none | none | 0.19 | 0.02 | 1.83 | 0.59 | 12.3 | 24 | 61 | 27 |
| PAMPSA($\alpha\beta$) | none | none | 0.21 | 0.04 | 2.30 | 0.40 | 12.3 | 21 | 56 | 10 |
| PADDA($\beta$) | none | none | 1.66 | 0.02 | 0.27 | 0.03 | 14.1 | −16 | 41 | 11 |
| PMA($\alpha$) | KOK | none | 0.21 | 0.01 | 2.66 | 0.36 | 12.1 | 16 | 70 | 14 |
| PAA($\alpha$) | KOK | none | 0.21 | 0.06 | 2.24 | 0.34 | 16.4 | 34 | 82 | 4 |
| PSS($\alpha$) | KOK | none | 0.25 | 0.03 | 2.53 | 0.39 | 16.4 | 53 | 76 | 13 |
| PAMPSA($\alpha\beta$) | KOK | none | 0.71 | 0.10 | 2.11 | 0.38 | 15.4 | 39 | 76 | 15 |
| PADDA($\beta$) | KOK | none | 1.38 | 0.04 | 0.25 | 0.02 | 5.1 | 5 | 21 | 15 |
| PMA($\alpha$) | KOK | Yes | 0.23 | 0.07 | 2.72 | 0.03 | 16.5 | 21 | 39 | 9 |
| PAA($\alpha$) | KOK | Yes | 0.24 | 0.08 | 2.58 | 0.33 | 15.5 | 14 | 67 | 3 |
| PSS($\alpha$) | KOK | Yes | 0.30 | 0.12 | 2.18 | 0.15 | 14.4 | 25 | 54 | 9 |
| PAMPSA($\alpha\beta$) | KOK | Yes | 0.71 | 0.05 | 2.21 | 0.55 | 13.4 | 21 | 49 | 2 |
| PADDA($\beta$) | KOK | Yes | 0.37 | 0.09 | 1.97 | 0.71 | 17.5 | 14 | 44 | 5 |
| none | None | Yes | 0.21 | 0.01 | 2.47 | 0.17 | 11.2 | 20 | −29 | 12 |
| none | KOK | Yes | 0.21 | 0.05 | 3.01 | 0.00 | 11.5 | 33 | −27 | 16 |
| none | PEG | Yes | 0.17 | 0.05 | 2.60 | 0.35 | 10.8 | 25 | −21 | 12 |
| none | PPG | Yes | 0.38 | 0.05 | 2.31 | 0.09 | 10.5 | 23 | −22 | 16 |
| none | none | none | 0.36 | 0.04 | 0.40 | 0.03 | 0.0 | 0 | 0 | 15 |

Example 2

Optimization of Coating

An optimization of the coating composition with PAA was conducted. The experimental procedures and measurements were the same as those in Example 1 except BSA (bovine serium albumin) was used as a blocking agent. The experimental results are shown in Table 2.

polymers increase the electrostatic bindings of negative molecules but greatly decrease the positive electrostatic binding of positive molecules. Since positive electrostatic binding directly correlates to protein binding, coatings containing PADDA has a lower protein binding. Surprisingly, PADDA reduces protein binding to the membrane without hurting the dendrimer's binding (see light output). Cationic ($\beta$) polyelectrolyte polymers can be replaced with blocking proteins in basic media, e.g. BSA. BSA is able to decrease the positive

TABLE 2

| Charged polymer & charged type | Protein block | Nonionic polyether | Added Silicate present | Negative Electrostatic binding Ave | Negative Electrostatic binding SD | Positive Electrostatic binding Ave | Positive Electrostatic binding SD | Protein binding change from uncoated % | Increase light output, % | CV % |
|---|---|---|---|---|---|---|---|---|---|---|
| PAA($\alpha$) | none | KOK | None | 0.20 | 0.04 | 1.66 | 0.23 | 24 | 85 | 5 |
| PAA($\alpha$) | BSA | KOK | None | 1.27 | 0.04 | 1.57 | 0.44 | −14 | 64 | 6 |
| PAA($\alpha$) | none | KOK | Yes | 0.25 | 0.04 | 2.66 | 0.37 | 11 | 108 | 3 |
| PAA($\alpha$) | BSA | KOK | Yes | 0.94 | 0.04 | 2.55 | 0.56 | −17 | 102 | 3 |
| PAA($\alpha$) × 2 | BSA | KOK | Yes | 0.83 | 0.04 | 2.41 | 0.12 | −4 | 80 | 2 |
| none | none | none | none | 0.25 | 0.04 | 0.55 | 0.07 | 0 | 0 | 2 | electrostatic bindings of positive molecules and protein bindings. Non-ionic polymers can decrease light outputs when they are used alone (inhibiting capture phase bindings). Surprisingly, non-ionic polymers do not have this impact when they are used with polyelectrolyte polymers.

Non-ionic polyether blockers eliminate the electrostatic bindings of negative molecules caused by cationic (β) polyelectrolyte polymers. Surprisingly, the light outputs or capture phase bindings are not decreased. Cationic (β) polyelectrolyte polymers behave similarly as proteins. Therefore, the impact of non-ionic polyethers to proteins on membranes reduces the binding of additional molecules. Blocking proteins can be added to the membrane and coated with non-ionic polyether without impacting the dendrimer binding.

Silicate compounds increase the positive electrostatic bindings. However, when used alone without any polymers the light output is decreased. This result is surprised since the increased negative charge density should enhance the dendrimer binding (see light output). Using silicate compounds combined with any polyelectrolyte polymers (α,β, αβ and non-ionic) does enhance the dendrimer binding with the expected increases in charge density. While not limited to any theory, it is believed that the polymer prevents the silicate compound from being washed away. The coating heating at high temperatures can also help silicate to form a polymeric which is less likely to be soluble. A silicate compound when used with polymers does also unexpectedly reduce the variation of light output, making the capture phase bindings fewer variables. All coatings increase the hydrophilicity (surface energy) of the membrane.

In summary, electrostatic energy of the coated glass cellulose can be optimized to selectively bind the capture phase over other molecules. The signals are greater than those from glass and lower % CV in the 1-3 range is obtained without any need for additional blocking steps. The coating composition at pH>7.0 includes the anionic polyelectrolyte polymers for increased capture phase binding, the silicate compound for reducing variations in capture phase binding anon-ionic polyethers combined with the cationic polymers and proteins for pre-blocking. This combination is not expected by the actions of each component used separately.

Example 3

Assessment of Membrane Fiber Composition

A comparison of the spot size for dispensing a fixed volume across a set of absorbent materials was conducted by testing Streptavidin immobilized on blue latex (1%) in PBS as the capture phase and measured by calipers. The blue latex was used to measure droplet size. Spot size was measured by calipers in mm. The comparison of liquid spread of other absorbent composites to glass composites is shown in Table 3. The binder utilized for bound glass/glass cellulose was PVA fibers (polyvinyl alcohol) or polystyrene latex particles; the binders were melted on to create the bound glass/glass cellulose.

TABLE 3

| Absorbent materials | Manufacture/grade | Spread of 1 µL of 1% latex particles in PBS, mm | Shape of area on absorbent material |
|---|---|---|---|
| Bound glass cellulose | Whatman GF/CM30 | 3.3 | Circular |
| Bound glass | Whatman Fusion 5 | 4.9 | Oval |
| Unbound glass | Whatman Rapid Release 24Q | 3.1 | Polygon |
| Unbound cellulose | Whatman Filter Paper 185 | 18.4 | Circular |

TABLE 3-continued

| Absorbent materials | Manufacture/grade | Spread of 1 µL of 1% latex particles in PBS, mm | Shape of area on absorbent material |
|---|---|---|---|
| Nitro-cellulose | Whatman Pura Bind ASD PE Supported | 8.33 | Circular |
| Polyester woven | Spun Lace Fabric | Non absorbent | Bead |

The results indicate that the bound glass cellulose and bound glass give the best performance with least spread of the capture phase. These absorbent materials are may thus serve as capture phases.

Example 4

Assessment of Membrane Composition for Electrostatic Binding

Six types of absorbent glass composites (a.k.a. substrates, membranes or papers) were compared for non-specific binding (protein, dye) and the results are shown in Table 4. Under microscope (100×), all materials showed glass fibers to be in unstructured formations. A problem with these membranes was that the density of fibers varied from 60% to 100% within an area of 250 µm$^2$. This variation in density of fibers was reduced to 80 to 100% as the area was increased to 2.5 mm$^2$. However, outliers occurred with one out of every twenty areas of 2.5 mm$^2$ had density of fibers <80%.

Electrostatic binding to various membranes were measured by staining with dihydroxy-5',5"-dinitrophenyl-3,4,5,6-tetrabromo sulfonephthalein dye (DIDNTB). Duplicate 3/16" circles of the membrane were punched and placed into separate wells of a 96-well ELISA plate. The dye solution was made at 100 mg DIDNTB dye in 100 mL toluene. 200 µL of dye was assessed to each well and the plate was shaken for 10 minutes at room temperature, after which the dye was removed and the plate was washed with 200 µL PBS. Alternatively tetrabromophenol blue (TBPB) could be used at 250 mg in 70 mL water with 10 mL ethanol to measure electrostatic binding as described previously. The absorbance of the dye bound to the paper circle was read at 650 nm. Protein binding was measured by 3/16" circles of the membrane punched and placed into separate wells of a 96-well ELISA plate. Material types, physical properties, and electrostatic (dye) binding results are shown in Table 4.

TABLE 4

| Paper Grade | Category Types | Binder | Thickness µm | Liquid absorbance mg water/cm$^2$ | Dye binding Ave | SD |
|---|---|---|---|---|---|---|
| Fusion 5 | Bound glass | PMMA | 370 | 53.05 | 0.28 | 0.03 |
| F255-7 | Bound glass cellulose 1 | PVA | 273 | 36.41 | 0.24 | 0.03 |
| F255-3 | Bound glass cellulose 2 | PVA | 250 | 40.66 | 0.18 | 0.04 |
| GF-A | Unbound glass | None | 260 | 66.83 | 0.35 | 0.05 |
| 9674 | Bound glass cellulose 3 | PVA | 170 | 33.62 | 0.12 | 0.01 |
| GF/CM30VA | Bound glass cellulose 4 | PVA | 435 | 45.58 | 0.10 | 0.03 |

The results show that the bound and unbound glass gives the highest electrostatic binding. Glass is anionic surface with silicates ($SiO_2$) capable of binding capture phases with positive charges. The bound glass was bound with polymethyl methacrylate (PMMA) latex, providing additional anionic charge carboxylate ($CO_2^-$). The addition of non-ionic celluloses reduces dye binding (see example grade GF/CM 30, VA9674, 255-3).

Example 5

Assessment of Capture Phase on Binding to Glass Cellulose Membrane

The ability of four types of capture phase particles to make precise and uniform capture areas was measured. The capture spot size and uniformity were measured after pipetting 1 µL of the capture phase particles onto the bound glass cellulose (9674 in Table 4). The capture phase was applied as a liquid drop onto the membrane surface and allowed to absorb and dry. Capture phases tested included latex particles, agarose, magnetic particles and dendrimer. All capture phases were positively charged by virtue of their core structures or by coating with proteins, in this case, streptavidin.

All particles were labeled with streptavidin. Streptavidin immobilized on agarose, magnetic particles and blue latex (Sigma-Aldrich) was dissolved at 1% in PBS. Streptavidin immobilized on dendrimer (Siemens D02901061 E5) was dissolved at 0.35 mg/mL in PBS. Biotin labeled fluorescein 10 µL of a 1 mg/300 µL PBS stock was added to 500 µL capture phase particle solution. The capture phase particle solution within biotin labeled fluorescein was deposited at 1 µL on to the smooth side of the glass cellulose membrane. A blue LED was used to excite the fluorescein biotin to be visually and digitally recorded. The capture phase was air dried and the spread of 1 µL was measured for 20 spots using a digital caliper capable of measuring to 0.01 mm. Comparison of the four capture phases over the glass cellulose membrane is listed in Table 5.

TABLE 5

Mean spot size, mm

| Capture membrane spotted on | Streptavidin immobilized on blue latex | | Streptavidin immobilized on agarose | | Streptavidin immobilized on Mag | | Streptavidin immobilized on dendrimer | |
|---|---|---|---|---|---|---|---|---|
| smooth side | Mean | SD | Mean | SD | Mean | SD | Mean | SD |
| Measured on rough (wire) side | 2.1 | 0.03 | 4.3 | 0.16 | 1.3 | 0.1 | 1.3 | 0.1 |
| Measure on smooth (felt) side | 1.7 | 0.1 | 4.3 | 0.1 | 1.3 | 0.1 | 1.3 | 0.1 |

The results indicate that the dendrimer and magnetic particles give the most precise and uniform capture area coatings.

Example 6

Assessment of Spotting Methodology

Glass bound membranes were spotted with capture phases using both piezo spotter and pin array techniques. The piezo spotter ejected out 0.104 nL droplet through a 100 µm nozzle at 22 mHz. The volume dispensed was controlled electronically by number of droplets fired. This experiment used a piezo pipette (Engineer Arts capillary piezo, Phoenix, Ariz.) and pin array equipment (Aurigin Technologies, Singapore). Pin spotting touched the glass bound membranes with one 100 nL spotted membrane and was done with 0.021 inch stainless steel pin spotter (0.5 mm) at a pitch distance of 1.5 mm.

Figure 1:
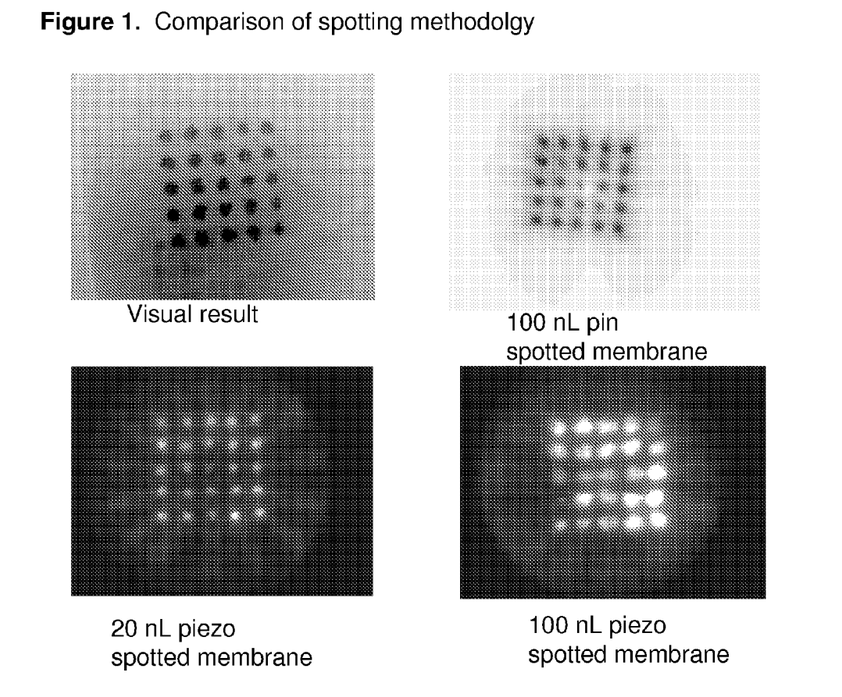
FIG. 1 shows the images of microarrays taken by an image recording device, a CCD camera for comparison of different spotting methodologies.

Spotting was done with dendrimer capture phase (Streptavidin dendrimer+Biotinylated D1 allergen). The spotting solution contained Amaranth dye and India ink for visualization of the spots. The dots were arrayed at 5 by 5 array pattern at 1.5 mm pitch on to the bound glass at 20 nL (192 drops) and 100 nL (960 drops). Each array was assayed by washing with 400 µL of wash buffer at 3 µL/sec. The spots were reacted with antibody to the allergen conjugated to alkaline phosphate enzyme. After 100 µL of chemiluminescent substrate was pipetted onto the washed membrane the response was immediately captured for 60 seconds in the CCD camera at 4×4 binning (See FIG. 1). Table 6 shows the comparison of spot variations using piezo and pin spotting techniques.

TABLE 6

|  | Run 1 | Run 2 | Run 3 |
|---|---|---|---|
| Dispense volume | 20 nL spots | 100 nL spots | 100 nL spots |
| Dispense mehod | Piezo | Piezo | Pin |
| Measured % CV | 24.4% | 21.9% | 16.4% |

In addition, spotting of blue latex-Streptavidin into 0.1" by 0.2" pad area demonstrated that the spots were arrayed at 4 by 8 patterns at 0.5 mm pitch on to the smooth sides of two types of glass cellulose membranes at 1.04 nL (10 drops). Visible inspections showed resolution of spots without touching each other.

The above experimental results show that the inconsistent light outputs are observed from both spotting methods. The pin method is less variable. The piezo spotting is better suited for dispense volume >25 nL, allowing higher density arrays. Piezo spotting also tends to generate more reactive outlier spots. Cleaning of the dispenser impacts the reproducibility of the array. Dendrimer and blue latex capture phases are both piezo friendly while only dendrimer capture phase is pin friendly. Latex and magnetic particles are not pin dispensing friendly.

Example 7

Assessment of Membrane Side

Membrane based on glass and cellulose fibers were made on paper making machines using a wire mesh. The surface that touches the wire mesh is "rough" to the touch. The surface away from the wire mesh is "felt" to the touch. The impact of capture membrane side on dispensing and reading out was measured using 1 µL of streptavidin immobilized on to blue latex. The capture phase was air dried. The spot size (mm) and uniformity (SD) were measured. Two membranes were assessed: one was a bound glass membrane and the other one was a bound glass cellulose membrane. The glass cellulose membrane was also tested after being coated with KOK and PADDA as non-specific blockers. Table 7 shows the comparison of spot variations based on membrane sides.

TABLE 7

| Absorbent materials | Deposited on the | Mean · mm Spread of 1 μL | | | |
|---|---|---|---|---|---|
| | | Measured on smooth (felt) side | | Measured on rough (wire) side | |
| | | Ave | SD | Ave | SD |
| Bound glass cellulose 3 | Smooth (felt) side | 1.4 | 0.1 | 3.1 | 0.4 |
| Bound glass cellulose 3 | Rough (wire) side | 3.5 | 0.7 | 2.3 | 0.2 |
| Bound glass | Smooth (felt) side | 1.6 | 0.5 | 1.9 | 0.5 |
| Bound glass | Rough (wire) side | 2.1 | 0.7 | 1.1 | 0.5 |
| Bound glass cellulose 3 with non-specific blocker | Smooth (felt) side | 1.7 | 0.1 | 2.1 | 0.03 |
| Bound glass cellulose 3 with non-specific blocker | Rough (wire) side | 2.5 | (0.1) | 2.4 | 0.2 |

The results show that the capture phases spread less when deposited on the smooth sides for all absorbent materials. The capture phases generally spread out when moving through the membranes. Coating the membranes with non-specific blockers reduces the spreading.

Example 8

Assessment of Surface Tension

Surface energies (dyne/cm) were measured using a VCA optima contact angle meter for the solutions used for adhesion (spotting) of the capture phases onto the membranes. The meter pipettes 4 μL of liquid onto a glass slide (Pearl 7101) so that the water contact angle could be measured. Water was used as a reference (72.80 dyne/cm). The comparison of the surface energies of the coating solutions used for spotting capture phases is shown in Table 8.

TABLE 8

| Coating solution | Composition | dyne/cm |
|---|---|---|
| Spotting buffer | 0 mM Tris, 6% BSA, 0.1M NaCl (pH 8.0) | 75.63 |
| Spotting buffer with trehalose | 0 mM Tris, 6% BSA, 0.1M NaCl (pH 8.0), 20% Trehalose | 59.28 |
| Phosphate buffer | 20 mM Tris buffer + 0.1M NaCl (pH 8.0) | 61.55 |
| Tris buffer | 20 mM Phosphate buffer + 0.1M NaCl (pH 7.0) | 59.67 |

The biological buffers used for spotting had a surface energy range of 59-76 dyne/cm (See Table 8). Literature values for the surface energies (dyne/cm) of proteins (albumin, IgG and fibrinogen are 69.7, 67.7 and 63.2 dyne/cm, respectively) also show that these proteins are high energy hydrophilic materials (~66.7 dyne/cm). Literature values for the surface energies (dyne/cm) of celluloses are around 44-55 or average of 49 dyne/cm. Measured surface energies (dyne/cm) of glasses are lower around 33-40 or average of 37 dyne/cm.

The non-electrostatic adhesion binding of the proteins can be expressed as the free energy of adhesion:

$$0 > \gamma_{protein-surface} - \gamma_{protein-liquid} - \gamma_{surface-liquid}$$

This equation is reorganized and can also be expressed as:

$$\gamma_{surface-liquid} > \gamma_{protein-surface} - \gamma_{protein-liquid}$$

wherein $\gamma_{surface-liquid}$ is the difference between the surface energy of the membrane and the surface energy of the bulk liquid (spotting liquid or sample); $\gamma_{protein-surface}$ is the difference between the surface energy of the particles and the surface energy of the membrane; and $\gamma_{protein-liquid}$ is the difference between the surface energy of the particles and the surface energy of the bulk liquid.

In practice, it has been found that the proteins are more adhered to the membranes when the surface energy of the membrane is increased (becomes more hydrophilic with lower contact angle). Alternatively the proteins are more adhered to membranes when the surface energy of the liquid is decreased (becomes more hydrophobic with high contact angle).

Example 9

Assessment of Non-Specific Blockers

Non-specific binding to capture membranes can be reduced by polymer coatings that reduce (block) the electrostatic adhesions of proteins to a surface. The use of propylene glycol (KOK, PEG) as polymer coating can serve as a non-specific blocker. It is generally known that proteins themselves such as albumin, fish gelatin and casein B can be used as anon-specific blockers like polyethylene glycol (PEG, TWEEN® 20).

The impact of glass cellulose membrane and the coating solution on the spot signal and noise was measured on the glass cellulose coated with KOK and PDDA, and KOK and PADDA. Smooth sides were used. Spotting was carried out with ALP-Biotin:Streptavidin-dendrimer. The spotting solution was made by diluting streptavidin-dendrimer capture phase (1.71 mg/mL) at 1:4 in the adhesion solution (See Example 8). The spotting was then mixed 1:1 with the solution of 2.5 μM biotinylated alkaline phosphatase in 50 mM HEPES, pH 7.0, 0.1 M NaCl, 1.5% BSA, 5 mM magnesium acetate and 0.5 mM zinc chloride and incubated for more than 5 minutes before spotting.

Figure 2:
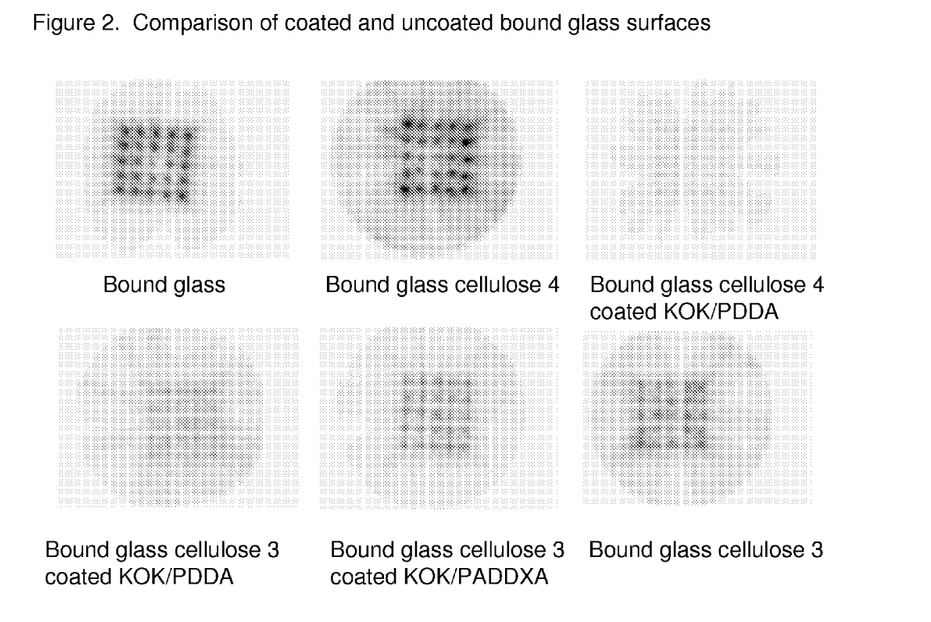
FIG. 2 shows the images of microarrays taken by the image recording device, a CCD camera for comparison of the coated and uncoated bound glass and glass cellulose surfaces.

Microarrays were made using the spin spotter/wash system and the smooth sides of the membrane. The dots were arrayed at 5 by 5 array pattern at 1.5 mm pitch on to the bound glass at 100 nL. After spotting the membrane was dried with desiccant for at least about 30 minutes. Each array was assayed by being washed twice with 400 μL of 20 mM Tris, pH 7.0, 0.9% NaCl, 1 mM magnesium acetate and 0.1 mM zinc chloride at 3 μL/sec. After 100 μL of chemiluminescent substrate was pipetted onto the washed membrane the response was immediately captured for 60 seconds in the CCD camera at 4×4 binning (See FIG. 2). Table 9 shows the comparison of capture membranes and coating solutions to signal and noise.

TABLE 9

| Solution | Surface energy dynes/cm | Capture membrane | Hydrophilic polymer blocking | Electrostatic dye binding | | Surface energy Dynes/cm | Light output | CV % |
|---|---|---|---|---|---|---|---|---|
| | | | | Ave | SD | | | |
| Spotting buffer | 75.63 | Bound glass | none | 0.28 | 0.03 | 37 | 213793 | 15.3 |
| Spotting buffer with trehalose | 59.28 | Bound glass | none | 0.28 | 0.03 | 37 | 211295 | 12.1 |

TABLE 9-continued

| Solution | Surface energy dynes/cm | Capture membrane | Hydrophilic polymer blocking | Electrostatic dye binding Ave | SD | Surface energy Dynes/cm | Light output | CV % |
|---|---|---|---|---|---|---|---|---|
| Phosphate buffer | 61.55 | Bound glass | none | 0.28 | 0.03 | 37 | 253095 | 20.4 |
| Tris buffer | 59.67 | Bound glass | none | 0.28 | 0.03 | 37 | 152159 | 26.6 |
| Spotting buffer | 75.63 | Bound glass cellulose 4 | none | 0.12 | 0.01 | 49 | 161282 | 15.6 |
| Spotting buffer with trehalose | 59.28 | Bound glass cellulose 4 | none | 0.10 | 0.03 | 49 | 121093 | 24.7 |
| Phosphate buffer | 61.55 | Bound glass cellulose 4 | none | 0.10 | 0.03 | 49 | 241987 | 41.9 |
| Tris buffer | 59.67 | Bound glass cellulose 4 | none | 0.10 | 0.03 | 49 | 199399 | 33.6 |
| Spotting buffer | 75.63 | Bound glass cellulose 4 | KOK and PDDA | 0.05 | 0.03 | 61 | 88546 | 11.5 |
| Spotting buffer | 75.63 | Bound glass cellulose 4 | KOK and PDDA | 0.06 | 0.03 | 62 | 127310 | 13.1 |
| Spotting buffer | 75.63 | Bound glass cellulose 3 | none | 0.10 | 0.03 | 38 | 275191 | 19.9 |
| Spotting buffer | 75.63 | Bound glass cellulose 3 | KOK and PDDA | 0.06 | 0..03 | 68 | 36182 | 13.4 |

In Table 9, light output is represented as relative light intensity by image analysis of a black and white picture where white reflectance is measured from black background.

The results show that the membranes with greater electrostatic binding hold the capture phases better with more signals due to being on the surface and lower variation due to less spreading. This can be seen by comparing glass to glass cellulose. Use of non-specific blockers decreases the electrostatic adhesion to capture phase just as they do for protein. This can be seen by comparing the formulas with KOK to those without KOK. In practice the blocking must be applied after spotting with capture phases.

The results also indicate that there is no correlation between the surface energies of the capture phases (compare with and without KOK) with more signals and lower variations. This supports that the capture phase (dendrimer) is bound by electrostatic charges. Capture phase binding is not improved as the surface energy of the coat solution is decreased.

Thus, in accordance with the present invention, there has been provided a coated substrate for capture phase binding, as well as methods of producing and using same, that fully satisfy the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A substrate for fabricating a biological microarray, the substrate comprising:
a support having an upper surface; and
a first coating applied to the upper surface of the support, wherein the first coating comprises a charged polymer and a silicate compound, and
a second coating comprising a non-ionic polyether.

2. The substrate of claim 1, wherein the first and second coatings are substantially uniformly applied to the upper surface of the support.

3. The substrate of claim 1, wherein the charged polymer is an anionic polyelectrolyte polymer.

4. The substrate of claim 3, wherein the anionic polyelectrolyte polymer is selected from the group consisting of polyacrylic acids, poly-(sodium-4-styrenesulfonates), polymethacrylic acids, polymethacrylic methacrylates and combinations thereof.

5. The substrate of claim 3, wherein the anionic polyelectrolyte polymer is selected from the group consisting of phosphate, carbonate, sulfonate polymers in ionized forms, and combinations thereof.

6. The substrate of claim 1, wherein the charged polymer is a cationic polyelectrolyte polymer.

7. The substrate of claim 6, wherein the cationic polyelectrolyte polymer is selected from the group consisting of poly (diallydimethylammonium chloride), polyethylenimine, polyvinylpyrrolidone, poly(acrylamide), poly(acrylamide-co-diallydimethylammonium chloride), polyvinylamine and combinations thereof.

8. The substrate of claim 6, wherein the cationic polyelectrolyte polymer is a blocking protein.

9. The substrate of claim 8, wherein the blocking protein is a casein or an albumin in a quaternary form with counter anions.

10. The substrate of claim 1, wherein the charged polymer is a zwitterionic polyelectrolyte polymer.

11. The substrate of claim 10, wherein the zwitterionic polyelectrolyte is poly(2-acrylamideo-2-methyl-l-propane-sulfonic acid).

12. The substrate of claim 1, wherein the non-ionic polyether is selected from the group consisting of polyethylene glycol, polypropyl glycol, polycarbonate polyether glycol and combinations thereof.

13. The substrate of claim 1, wherein the silicate compound is at least one of a metal silicate and an alkyl silicate.

14. The substrate of claim 13, wherein the metal silicate is an alkali metal silicate.

15. The substrate of claim 14, wherein the alkali metal silicate is sodium silicate.

16. The substrate of claim 1, wherein the support comprises glass.

17. The substrate of claim 1, wherein the support comprises a membrane.

18. The substrate of claim 17, wherein the membrane comprises at least one material selected from the group consisting of glass, cellulose, and glass cellulose.

19. The substrate of claim 1, wherein said support comprises glass or glass cellulose; said charged polymer is PDDA and said non-ionic polyether is KOK or PEG.

* * * * *